Figure 1:
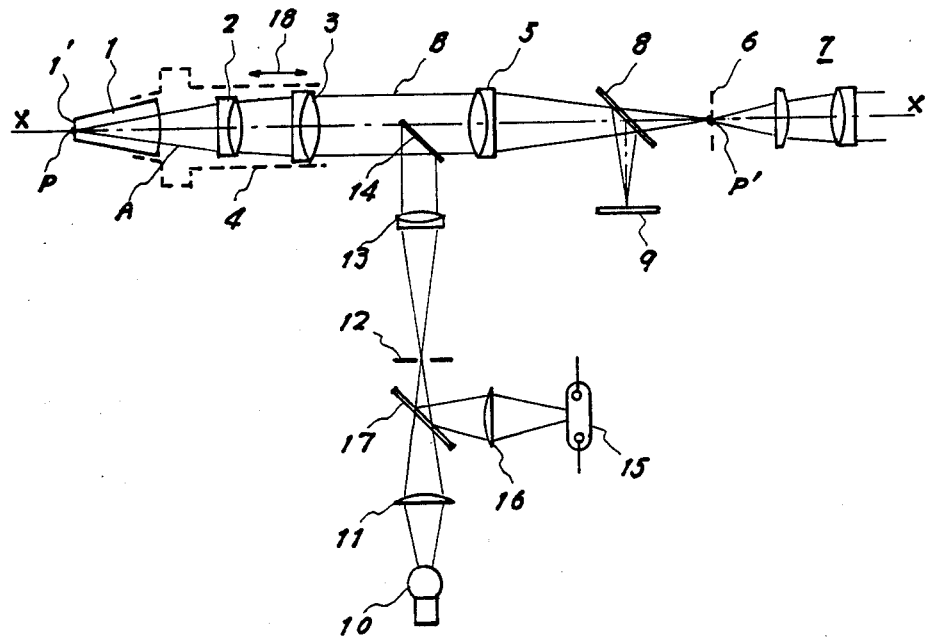

United States Patent [19]

Abe, Kumiomi et al.

[11] 4,209,225
[45] Jun. 24, 1980

[54] ADJUSTABLE MICROSCOPE FOR FOLLOWING AXIAL DISPLACEMENT OF AN OBJECT

[75] Inventors: Abe, Kumiomi; Susumu Fujita, both of Kobe, Japan

[73] Assignee: Konan Camera Research Institute, Kobe, Japan

[21] Appl. No.: 3,105

[22] Filed: Jan. 15, 1979

[30] Foreign Application Priority Data

Jan. 23, 1978 [JP] Japan .................................. 53/6542

[51] Int. Cl.² ........................ A61B 3/10; G02B 7/04; G02B 23/16
[52] U.S. Cl. ............................... 350/46; 350/236; 351/6; 351/16
[58] Field of Search ................. 350/46, 47, 91, 70, 350/78, 54, 55, 235, 236, 244, 255, 81; 351/6, 16

[56] References Cited

U.S. PATENT DOCUMENTS

| 2,705,490 | 4/1955 | Littman ................................. 350/91 |
| 4,023,189 | 5/1973 | Govignon ............................... 351/6 |

FOREIGN PATENT DOCUMENTS

943430  5/1956  Fed. Rep. of Germany ............. 350/54

Primary Examiner—Jon W. Henry
Attorney, Agent, or Firm—Eugene E. Geoffrey, Jr.

[57] ABSTRACT

A microscope for use in applications wherein the object to be observed may move in a path along the optical axis of the microscope which includes an objective lens, collimating lens for producing a parallel beam, and an imaging lens for focusing the parallel beam to form an image, the objective and collimating lenses being movable with the object being observed.

2 Claims, 2 Drawing Figures

ADJUSTABLE MICROSCOPE FOR FOLLOWING AXIAL DISPLACEMENT OF AN OBJECT

This invention relates to microscopes and more particularly to microscopes for use in cases wherein the object to be observed may move occasionally along the optical axis.

The object to be observed by a microscope is generally fixed with respect to the microscope frame and the image focus is adjusted by moving the lens system with respect to the fixed object. If the object moves along the optical axis, the adjusted focus will be upset immediately even if the movement is very small. However, in some microscope applications, the object to be observed may occasionally move and this movement can not generally be avoided. For example, a corneal endothelcell microscope is used for observation of the status of corneal endothelcells, which is required for diagnosis of corneal and other opthalmic diseases, examination of healing condition after corneal transplantation and the like. When using a prior art corneal endothelcell microscope, it is a general practice to apply a narcotic to the eye. The face is then pressed against a frame of the equipment and the top surface of the objective lens of the microscope is placed in contact with the eyeball. However, due to narcosis sensation paralysis of the eye, the patient can not sense whether or not the objective lens is in optimum contact condition with the eyeball by himself. This often results in excessive or insufficient pressure on the eyeball and, moreover, separation of the objective lens from the eyeball. Furthermore, the position of cornea varies constantly with variation of eye pressure and pulse. Excessive pressure may wound the eye and insufficient pressure will upset the imaging focus of the microscope. Thus, it has been usual that only several satisfactory photographs are obtained from as many as one hundred shots.

Accordingly, an object of this invention is to provide an improved microscope which can follow an object moving along the optical axis without change of its imaging point.

This object can be attained by an improved microscope according to this invention, which comprises objective means having a contact surface at the front end, which is placed in contact with an object to be observed, collimating means located in the rear of the objective means for converting a light beam coming through the objective means from a predetermined optical point adjacent to the contact surface into a parallel beam, and imaging means located in the rear of the collimating means for focusing the parallel beam to form an image of the optical point at a predetermined point. The objective means and collimating means are movable with respect to the imaging means in the axial direction. Means are provided for moving the objective means and collimating means together to such direction that the contact surface of the objective means comes into contact with the object to be observed.

Other objects and features of this invention will be described in more detail hereinunder with reference to the accompanying drawings.

IN THE DRAWINGS

Figure 2:
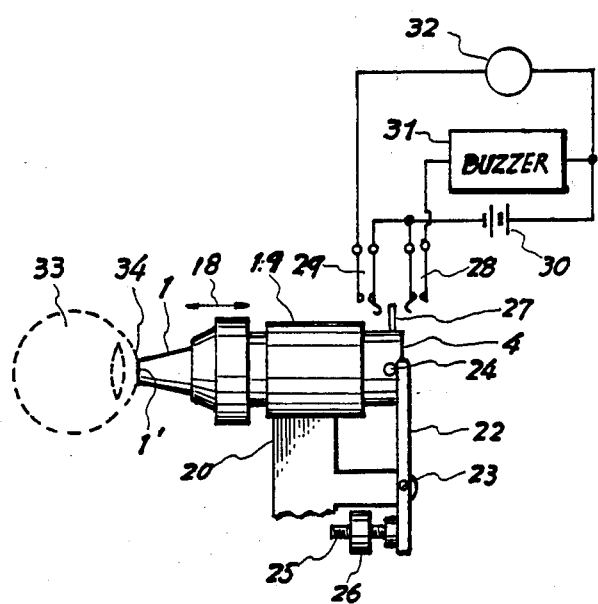

FIG. 1 is a schematic view representing an optical arrangement of an embodiment of the microscope of this invention, and FIG. 2 is a schematic view representing a part of the embodiment of FIG. 1 together with its electrical arrangement.

Throughout the drawings, like reference numerals are used to denote like structural components.

FIG. 1 shows a corneal endothelcell microscope embodying the principle of this invention. The microscope includes a conical objective lens 1 having a flat contact surface 1' at the front end. An intermediate lens 2 and a collimating lens 3 are located in this order in the rear of the objective lens 1. These lenses 1, 2 and 3 are contained in a common body tube 4 shown schematically in broken lines and arranged so that a light beam A from an optical point P adjacent to the contact surface 1' of the objective lens 1 leaves the collimating lens 3 as a parallel beam B.

After the collimating lens 3, there is provided an imaging lens 5 which focuses the parallel beam B from the collimating lens 3 to form an image P' of the optical point P on an image plane 6 as shown by the broken lines. This image is usually magnified by an eyepiece unit 7 provided in the rear of the image plane 6 for direct observation, or transferred onto a photographic plate or film 9 by a fixed semi-transparent mirror or detachable reflecting mirror 8 located between the imaging lens 5 and the image plane 6 for photographing.

As conventional in this field, the microscope includes as an attachment an illuminating optical system, which is composed of an incandescent lamp 10, a condenser lens 11, an iris 12, a collimating lens 13 and a reflecting mirror 14. The collimating lens 13 is arranged to provide a parallel incident light beam and the mirror 14 is arranged in a part of the parallel beam B to direct the parallel beam from the collimating lens 13 forwardly along the optical axis X and focus it onto the object at the optical point P. The system also includes a flashlight source 15, a condenser lens 16 and a reflecting mirror 17 which are used for photographing. A light beam from the light source 15 is reflected by the mirror 17 to follow the same path as the beam from the lamp 10 to illuminate the object.

As a feature of this invention, the body tube 4 containing the lenses 1, 2 and 3 is arranged to be movable along the optical axis as shown by an arrow 18 with respect to the imaging lens 5, so that the distance between the collimating lens 3 and the imaging lens 5 is variable. An embodiment of this movable structure will be described with reference to FIG. 2.

In FIG. 2, the body tube 4 of FIG. 1 is supported within a guide cylinder 19 fixed to an equipment frame element 20 so as to be movable in the axial direction as shown by the arrow 18. A number of steel balls (not shown) are arranged between the body tube 4 and the cylinder 19 so that friction between both is effectively reduced to facilitate the axial movement of the body tube 4. A lever 22 is vertically supported at an intermediate point by a pivor 23 provided on the frame 20. The front face of the upper end of the lever 22 faces the pin 24 projecting laterally from the body tube 4. A screw rod 25 extends forwardly from the lower end of the lever 22 and a weight 26 is screwed onto the rod 25 to provide a counterclockwise moment to the lever 22, in the drawing, so that the pin 24, and therefore, the body tube 4 are urged always to the forward direction. The pressure applied to the body tube 4 from the lever 22 may be about several grams per square centimeter for example and can be adjusted by moving the weight 26.

Another pin 27 extends from the body tube 4 and faces the actuating members of two normally open switches 28 and 29 located respectively in the rear and front thereof. The switch 28 is connected in series with a power supply 30 (shown as battery) and a buzzer 31 and the switch 29 is connected in series with the power supply 30 and an indication lamp 32. As readily noted, the switch 28 is closed by backward movement of the body tube 4, while the switch 29 is closed by forward movement thereof.

In observation, the face of a patient is placed in a position defined by a corresponding portion of the equipment frame 20 (though not shown in the drawing) and the contact surface 1' of the objective lens 1 is placed in contact with the cornea 34 of the eye 33 to be observed, with a small pressure applied by the weight 26 through the lever 22. Here, it can be understood that the body tube 4 follows a slight axial movement of the cornea 34, caused as aforementioned, with the above substantially constant contact pressure. Although such axial movement of the body tube 4 results in a variation of the distance between the collimating lens 3 and the imaging lens 5, this variation has no effect on the optical system due to parallelism of the beam B in this region. That is, no change occurs in illuminating, observing, imaging and photographing conditions.

In addition, the switch 28 closes to actuate the buzzer 31 when the eye approaches excessively, thereby alarming it before the eye is wounded. On the other hand, the switch 29 is closed to actuate the lamp 32 when the eye 33 goes away beyond the followable limit of the body tube 4, thereby indicating impossibility of observation or photographing.

The above description has been made for illustrative purpose only and it should be noted that various changes and modifications can be made by those skilled in the art without departing from the scope of this invention. For example, spring force, electromagnetic force and the like can be utilized for urging the body tube forwardly instead of the weight-level mechanism as shown. Moreover, the switches 28 and 29 can be replaced by one or more switches, which can be of mechanical, optical, electrical or any other known type, and the buzzer 31 and the lamp 32 can be replaced by any kind of indicating and alarm device which may be of either digital or analog type and can present any kind of information, which may be audible, visual or other sensitive type, regarding the movement of the body tube 4.

Furthermore, the above description has been made with reference to a corneal endothelcell microscope as an embodiment and it should be noted that this invention is not limited to this microscope application but is also applicable to other microscopes which are used for observing objects being subject to axial movement in the technical fields which are not only medical but also biological, engineering and others.

What is claimed is:

1. A microscope comprising objective lens means having a contact surface at the front end, which is to be placed in contact with an object to be observed, collimating means located to the rear of said objective lens means for converting a light beam coming through said objective lens means from a predetermined optical point adjacent to said contact surface of said objective lens means into a parallel beam, imaging means located to to the rear of said collimating means for focusing said parallel beam to form an image of said optical point at a predetermined position, said objective lens means and collimating means being fixedly positioned one relative to the other and axially movable with respect to said imaging means, and means for urging said objective lens means and collimating means together away from said imaging means and in the direction of said object, whereby said contact surface of said objective lens means is maintained in contact with the object to be observed and will follow axial movement of the object without displacement of the image from said predetermined position.

2. A microscope according to claim 1, wherein said microscope further comprises indicating means for responding to said axial movement of said objective lens means and collimating means and provides an indication of both excessive and insufficient contact pressure with said object.

* * * * *